(12) United States Patent
Yamage et al.

(10) Patent No.: US 6,184,687 B1
(45) Date of Patent: Feb. 6, 2001

(54) PLASMA PROCESS END POINT DETERMINATION METHOD AND APPARATUS, AND PLASMA EVALUATION METHOD AND APPARATUS

(75) Inventors: Masashi Yamage; Hiroyuki Takada, both of Yokohama; Takeshi Yamauchi, Tokyo, all of (JP)

(73) Assignee: Kabushiki Kaisha Toshiba, Kawasaki (JP)

( * ) Notice: Under 35 U.S.C. 154(b), the term of this patent shall be extended for 0 days.

(21) Appl. No.: 09/175,344

(22) Filed: Oct. 20, 1998

(30) Foreign Application Priority Data

Oct. 20, 1997 (JP) .................................................... 9-286344
Dec. 17, 1997 (JP) .................................................... 9-347801

(51) Int. Cl.$^7$ .................................................... G01N 27/62
(52) U.S. Cl. .................................................... 324/464; 324/678
(58) Field of Search .................... 324/464; 204/192.33, 204/192.34, 298.32; 216/60, 67, 77; 219/121.2, 121.26, 121.41; 250/492.2, 492.3; 356/222, 437

(56) References Cited

U.S. PATENT DOCUMENTS

| 4,493,745 | * | 1/1985 | Chen et al. | 156/626 |
| 4,602,981 | | 7/1986 | Chen et al. . | |
| 5,086,015 | * | 2/1992 | Itoh et al. | 437/173 |
| 5,463,219 | * | 10/1995 | Buckley et al. | 250/281 |

FOREIGN PATENT DOCUMENTS

| 61-53728 | 3/1986 | (JP) . |
| 61-256637 | 11/1986 | (JP) . |

* cited by examiner

*Primary Examiner*—Safet Metjahic
*Assistant Examiner*—Etienne P LeRoux
(74) *Attorney, Agent, or Firm*—Oblon, Spivak, McClelland, Maier & Neustadt, P.C.

(57) ABSTRACT

A plasma process end point determination method comprises the steps of measuring a physical quantity in a circuit for producing a plasma within a reaction chamber, and determining a plasma process end point on the basis of an inflection point of the measured physical quantity in relation to the passing of time.

32 Claims, 9 Drawing Sheets

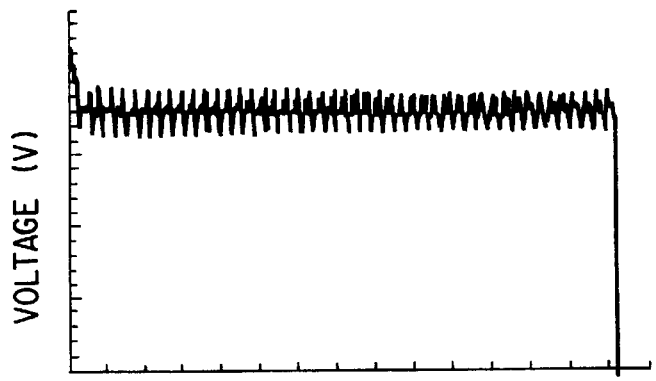
F I G. 1
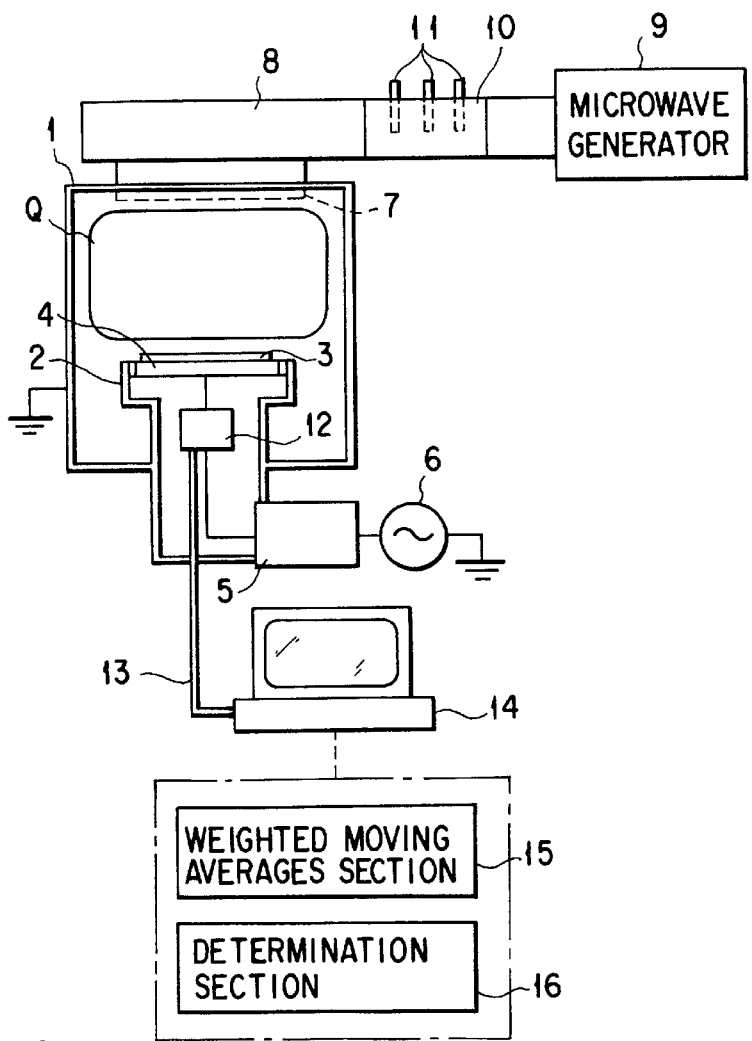
F I G. 2

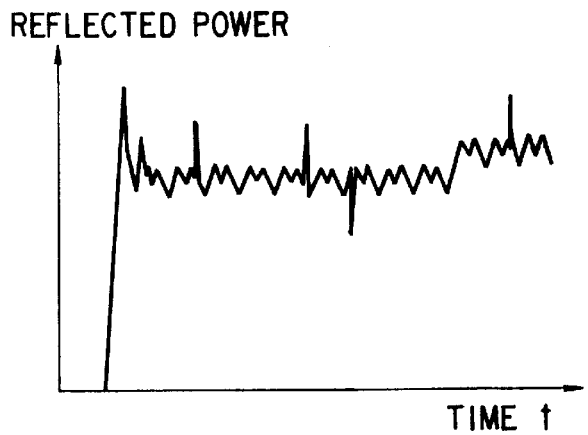
F I G. 5
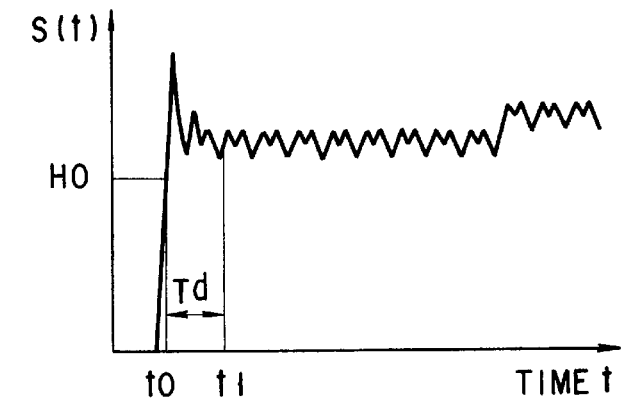
F I G. 6
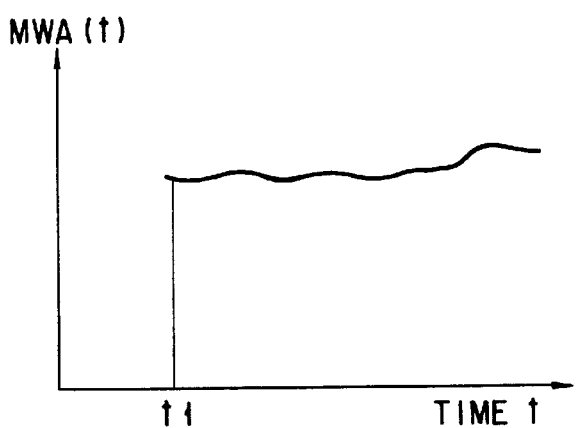
F I G. 7
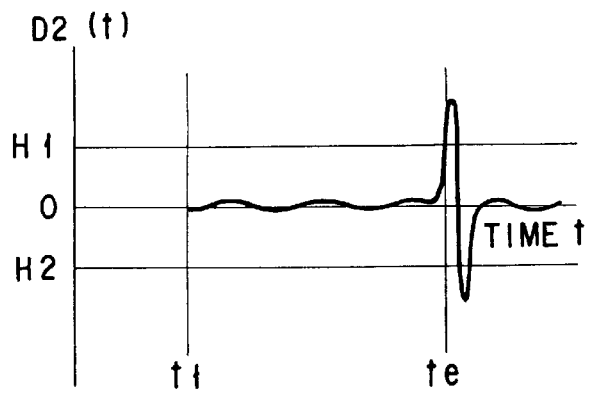
F I G. 8

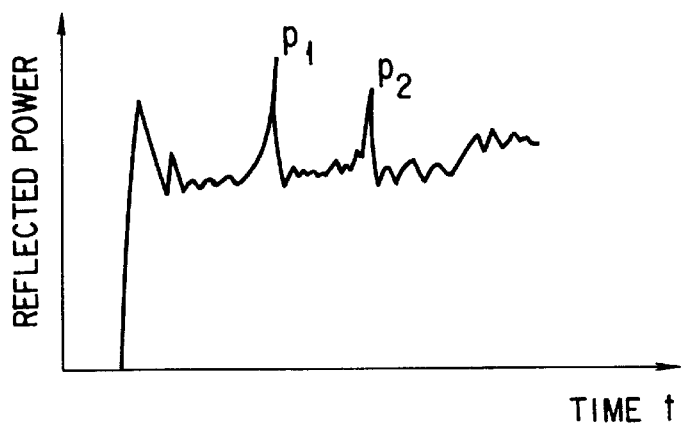
F I G. 13
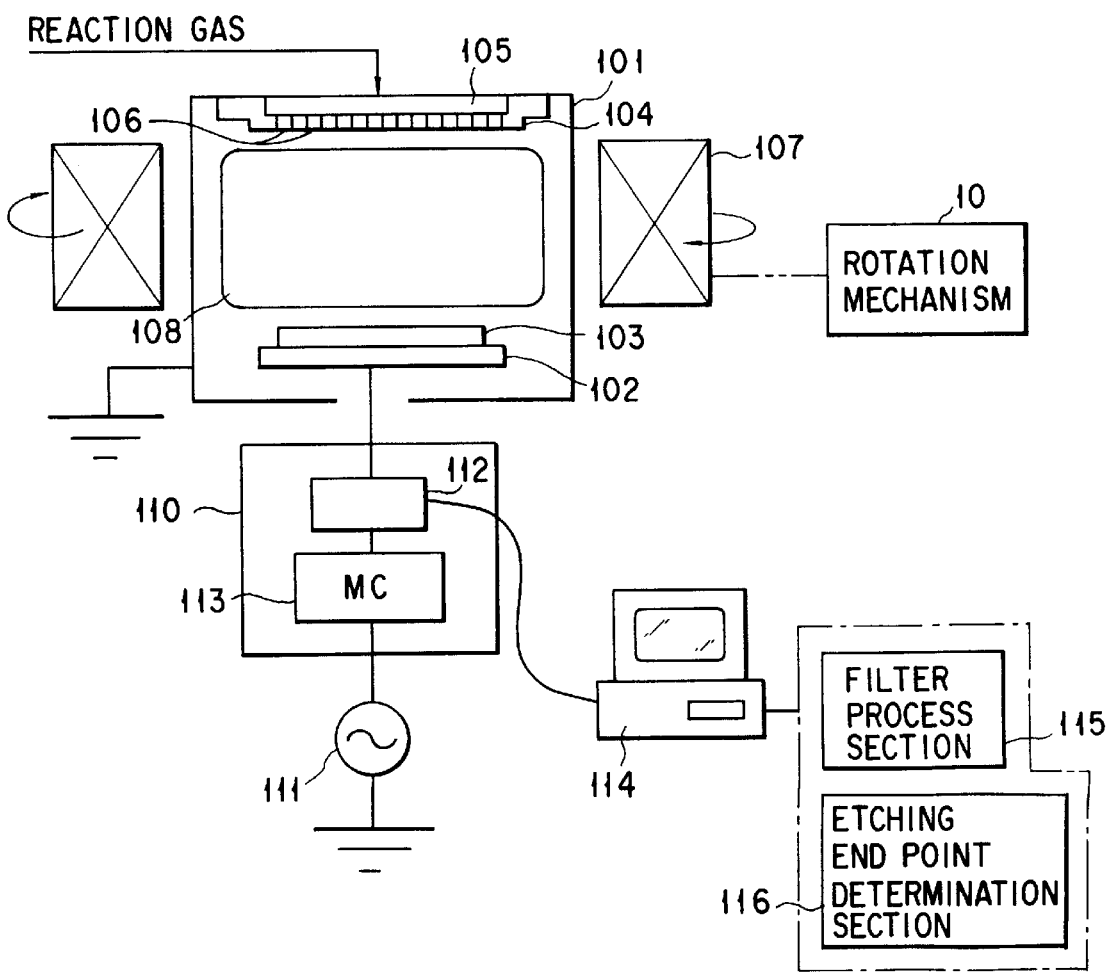
F I G. 14

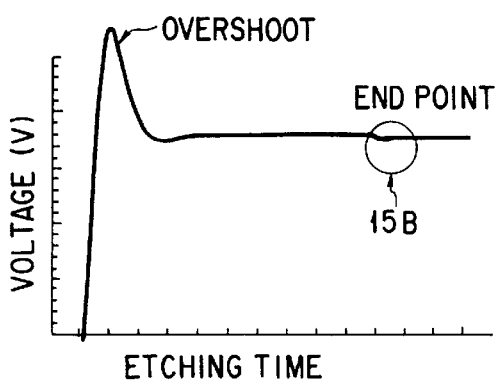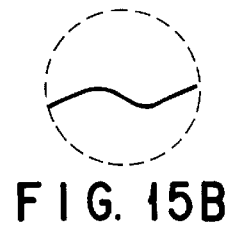
FIG. 15A  FIG. 15B
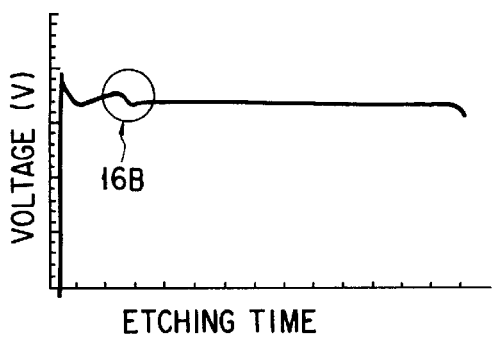
FIG. 16A  FIG. 16B
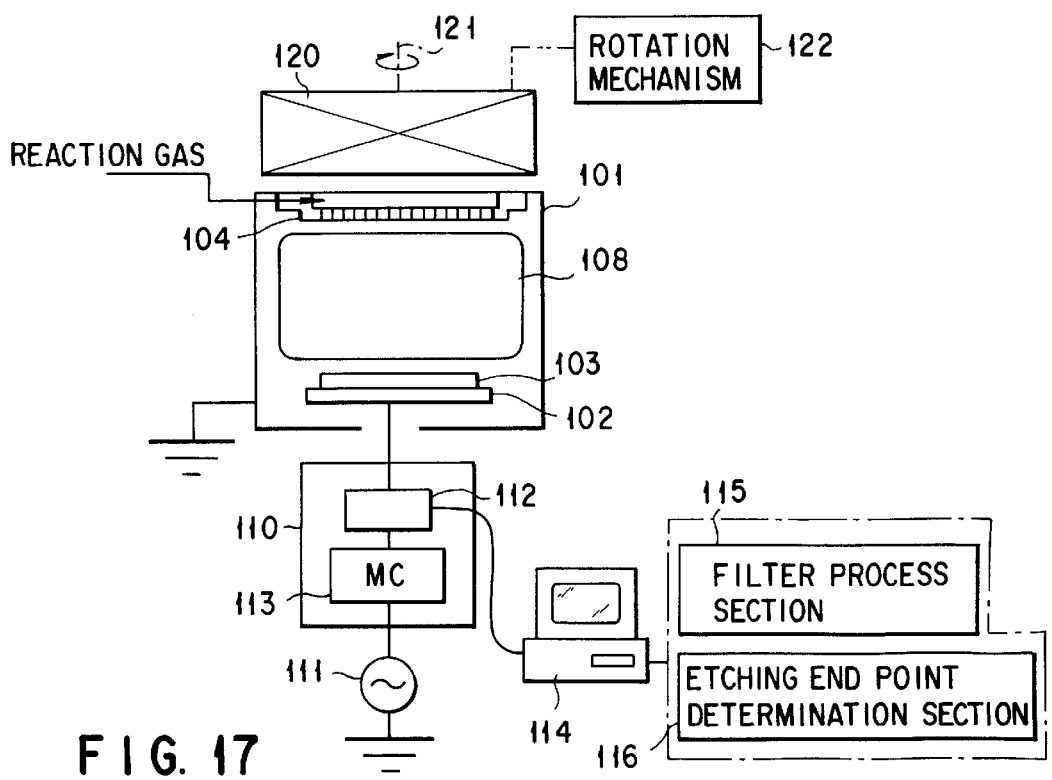
FIG. 17

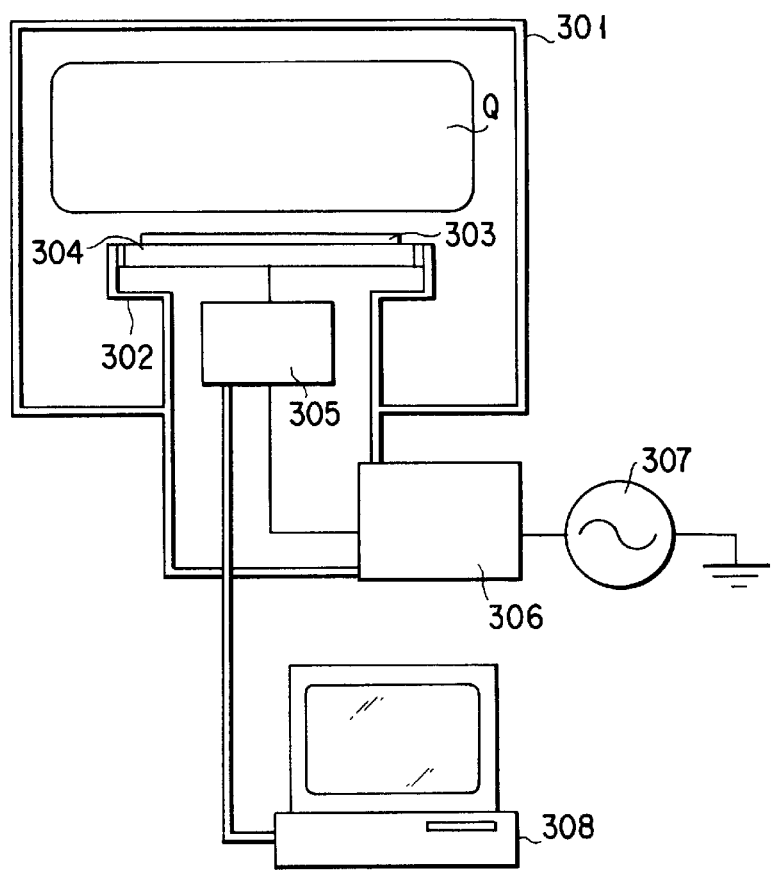
F I G. 18
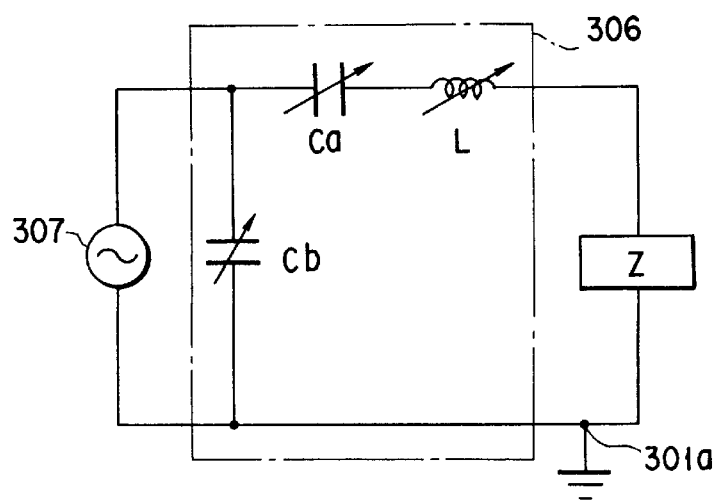
F I G. 19

PLASMA PROCESS END POINT DETERMINATION METHOD AND APPARATUS, AND PLASMA EVALUATION METHOD AND APPARATUS

BACKGROUND OF THE INVENTION

The present invention relates to a plasma process end point determination method and apparatus for determining an end point of a plasma process in a case where an etching process, etc. is performed by producing a plasma within a reaction chamber with use of either RF (radio-frequency) waves or microwaves or both.

The present invention also relates to a method and apparatus for evaluating the assembly reproducibility of a plasma process apparatus for carrying out an etching process, etc. by producing a plasma within a reaction chamber.

An emission spectroscopy method is widely adopted as one method of automatically determining the end of an etching or cleaning process on an object within a reaction chamber. In the emission spectroscopy method, an emission light intensity of a specific wavelength of plasma light, which is produced within the reaction chamber in accordance with the kind of etching gas, etc., is measured.

If a noise component is included in the light intensity of plasma light, it is removed by digital arithmetic operations in order to exactly determine the end point of etching or cleaning.

In an example of the method of determining the end of etching, with the noise component removed by digital arithmetic operations, a light intensity is digitally converted and sampled and a primary differential value of the sampling value is found from a moving average value of the sampling value. A secondary differential value of the sampling value is found from a difference in a moving average value of the primary differential value. A moving average value of the secondary differential value is compared with a preset value, whereby the end point of etching is determined.

However, in the method of determining the etching end point by using light intensity of the plasma, if a contamination lies on a plasma light take-in window provided at the reaction chamber, the contamination degrades transmissivity of plasma light and adversely affects the determination of the etching end point. In addition, flickering of plasma light due to instability of plasma adversely affects the determination of the etching end point.

Moreover, when an object of a novel material is etched, it is necessary to find a light intensity of plasma, which is enough to detect the etching end point, and a specific wavelength having a variation range.

Since the noise component is removed by finding moving averages twice or more, a time at which a signal variation occurs at the etching end point will delay after arithmetic operations, as compared to the state before the arithmetic operations. As a result, it becomes difficult to exactly determine the etching end point.

One example of the etching apparatus is a magnetron reactive ion etching (RIE) apparatus using a magnetron. In the magnetron RIE apparatus, the magnetron is rotated near the reaction chamber while RF power is supplied into the reaction chamber, and a plasma is produced within the reaction chamber to etch an object to be treated.

According to an etching end point determination method for this etching apparatus, a light intensity of plasma within the chamber is monitored through a light pass window, generally formed of quartz glass, and a variation point of the plasma light intensity is determined as an etching end point.

However, a variation point of plasma light intensity cannot be determined where the light pass window for monitoring plasma light intensity is contaminated or an area for etching is small due to a shift of a plasma caused by rotation of the magnetron, for example, where the area for etching is 10% or less of the entire area of an 8-inch semiconductor wafer, that is, the opening ratio is 10% or less.

In order to solve the above problems, an etching end point determination method has recently been adopted in which the plasma is regarded as part of a RF circuit and an impedance of the plasma is detected, and a variation point of the impedance is determined as etching end point.

However, in this method, too, the impedance varies at a rotational cycle of the magnetron due to fluctuations of the plasma caused by rotation of the magnetron. If the etching area is 10% or less as mentioned above, it is difficult to determine the etching end point because a variation of the etching end point is minute.

For example, FIG. 1 shows an RF voltage waveform detected by an RF circuit. The RF voltage waveform varies in accordance with the rotational cycle of the magnetron, and a minute variation of impedance at the etching end point cannot be recognized owing to noise at the rotational cycle of the magnetron. As a result, the etching end point cannot be determined.

As has been described above, the impedance varies at the rotational cycle of the magnetron due to fluctuations of plasma caused by the rotation of the magnetron, and if the process area is small, the process end point cannot be determined because the variation of the end of a plasma process such as an etching process is minute In the plasma process apparatus, if objects are etched or ashed for a long time, products or products by reaction gas, which are produced by the etching or ashing, are deposited as films on the electrodes, parts constituting the electrodes and the inner wall surface of the reaction chamber. In addition, coating material on the electrodes and inner wall of the reaction chamber may be removed, and a uniform plasma process cannot be performed and come off deposit materials become particles. In order to solve these problems, the electrodes and reaction chamber are cleaned periodically and the electrodes and parts constituting the electrodes are exchanged periodically.

In order to clean the electrodes and reaction chamber and to exchange the electrodes and parts constituting the electrodes, the electrodes need to be disassembled and reassembled. In this case, if the states of the reassembled electrodes, etc. differ from the states before disassembly, a predetermined plasma process performance cannot be attained thereafter.

Under the circumstances, in the prior art, in order to evaluate the plasma process performance after the disassembly/reassembly of the electrodes, etc., a predetermined sample is subjected to the same plasma process as the actual one and the state of the processed sample is evaluated for adjustment.

However, in the method of subjecting the sample to the plasma process and evaluating the state of the processed sample for adjustment, since the state of the sample is evaluated, the evaluation method becomes an indirect one. Moreover, since the sample needs to be subjected to the same plasma process as the actual one, a long time is needed for the process.

In particular, if it is found from a sample evaluation result that a predetermined plasma process performance is not obtained, the plasma process performance of the sample has to be evaluated once again after the adjustment. This evaluation may be repeated until the predetermined plasma process performance is attained. Consequently, a longer time is needed, more samples are needed, and the cost increases.

BRIEF SUMMARY OF THE INVENTION

An object of the present invention is to provide a plasma process end point determination method and apparatus capable of exactly determining a plasma process end point such as an etching end point, without influences of contamination on a plasma light take-in window or flickering of plasma light, and with less influences of a time delay occurring when moving averages are found twice or more or a signal variation is minute.

Another object of the invention is to provide a plasma process end point determination method and apparatus capable of determining a plasma process end point without influences of noise due to rotation of a magnetron.

Still another object of the invention is to provide a time-saving, cost-effective plasma evaluation method and apparatus for a process apparatus, which directly evaluate a plasma process performance, without using a sample.

In order to achieve the above object, according to a first aspect of the invention, there is provided a plasma process end point determination method, comprising the steps of:
 measuring a physical quantity in a circuit for producing a plasma within the reaction chamber; and
 determining a plasma process end point on the basis of an inflection point of the measured physical quantity in relation to the passing of time.

According to a second aspect of the invention, there is provided a plasma process end point determination apparatus, comprising:
 physical quantity measurement means for measuring a physical quantity in a circuit for producing a plasma within the reaction chamber; and
 plasma process end point determination means for determining a plasma process end point on the basis of an inflection point of the physical quantity measured by the physical quantity measurement means in relation to the passing of time.

According to a third aspect of the invention, there is provided a plasma process end point determination method, comprising the steps of:
 detecting a physical quantity in a circuit for generating a plasma within the reaction chamber as a detection signal;
 filtering the detection signal and passing a component of the detection signal, which has a frequency lower than a rotational frequency of a magnetron; and
 determining an end point of a plasma process for an object on the basis of a signal variation of the filtered detection signal.

According to a fourth aspect of the invention, there is provided a plasma process end point determination apparatus, comprising:
 detection means for detecting a physical quantity in a circuit for generating a plasma within the reaction chamber as a detection signal;
 filter process means for filtering the detection signal detected by the detection means and passing a portion of the detection signal which has a frequency lower than a rotational frequency of a magnetron; and
 plasma end point determination means for determining an end point of a plasma process for an object on the basis of a variation of the detection signal filtered by the filter process means.

According to a fifth aspect of the invention, there is provided a plasma evaluation method, comprising the steps of:
 detecting a physical quantity in a circuit for producing a plasma within a reaction chamber; and
 comparing the detected physical quantity with a preset value, thereby evaluating the condition of produced plasma.

According to a sixth aspect of the invention, there is provided a plasma evaluation apparatus, comprising:
 a plasma producing circuit for producing a plasma within the reaction chamber;
 physical quantity measuring means for measuring a physical quantity in the plasma producing circuit; and
 evaluation means for evaluating the condition of the produced plasma by comparing the physical quantity measured by the physical quantity measuring means with a preset value.

According to a seventh aspect of the invention, there is provided a plasma evaluation apparatus comprising:
 a plasma producing circuit for generating a plasma within a reaction chamber;
 a matching circuit for establishing matching between the plasma producing circuit and the reaction chamber;
 physical quantity measuring means for measuring a physical quantity in the matching circuit; and
 evaluation means for evaluating the condition of the produced plasma by comparing the physical quantity measured by the physical quantity measuring means with a preset value.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a graph showing a radio-frequency (RF) voltage waveform detected from an RF circuit of a conventional plasma process end point determination apparatus;

FIG. 2 is a plasma process end point determination apparatus according to a first embodiment of the present invention;

FIG. 5 shows an example of a waveform of a sampling value of reflected power;

FIG. 6 shows a signal obtained by passing a sampling value of a measured signal through a median filter and removing peculiar peaks therefrom;

FIG. 7 shows an example of a waveform of a sampling value MWA(t) which has been subjected to a weighted moving averaging;

FIG. 8 shows a secondary differentiation value of the sampling value MWA(t) which has been subjected to a weighted moving averaging;

FIG. 13 shows a specific pattern variation appearing due to a plasma abnormal discharge or defective plasma process;

FIG. 14 shows an etching end point determination apparatus according to a fourth embodiment of the invention;

FIG. 15A shows an RF voltage waveform detected by a probe;

FIG. 15B shows the RF voltage waveform detected by the probe;

FIG. 16A shows an RF voltage waveform obtained after a second filter process;

FIG. 16B shows the RF voltage waveform obtained after the second filter process;

FIG. 17 shows an etching end point determination apparatus according to a fifth embodiment of the invention;

FIG. 18 shows a plasma evaluation apparatus according to a sixth embodiment of the invention;

FIG. 19 shows an equivalent circuit of a matching circuit used in the apparatus shown in FIG. 18;

DETAILED DESCRIPTION OF THE INVENTION

Figure 3:
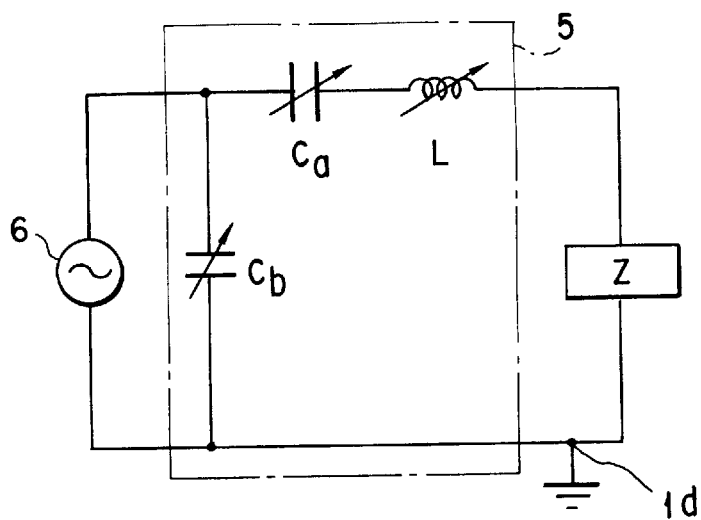
FIG. 3 is an equivalent circuit of a matching circuit used in the apparatus shown in FIG. 2.

Embodiments of the present invention will now be described with reference to the accompanying drawings.
First Embodiment According to a plasma process end point determination apparatus of a first embodiment of the invention, when a plasma process end point in a process of producing a plasma within a reaction chamber and processing an object is to be determined, a physical quantity in a circuit for producing the plasma is measured and the plasma process end point is determined on the basis of an inflection point of the physical quantity with the passing of time.

Specifically, in the plasma process end point determination apparatus of this embodiment, a measurement signal obtained by measuring the physical quantity in the circuit for producing the plasma is passed through a median filter. The measurement signal which has been passed through the median filter is subjected to a weighted moving averaging process in accordance with a Gauss distribution. A primary differential value or a secondary differential value of the measurement signal, which has been subjected to the weighted moving averaging process, is found and compared with a predetermined threshold value. Thus the plasma process end point is determined.

FIG. 2 shows a plasma process end point determination apparatus according to the first embodiment of the invention.

As is shown in FIG. 1, a table 2 is disposed within a reaction chamber 1. A semiconductor wafer 3 or an object to be processed is placed on the table 2. The semiconductor wafer 3 is not a sample of an actual product, but is a wafer for use in determining the plasma process end point.

A reaction gas such as an etching gas is supplied into the reaction chamber 1.

A discharge electrode 4 is provided on the table 2 of reaction chamber 1. A radio-frequency (RF) power supply 6 is connected to the discharge electrode 4 via a matching circuit 5, thus constituting an RF circuit. That is, the RF circuit for producing a plasma in the reaction chamber comprises the discharge electrode 4, matching circuit 5 and RF power supply 6. The RF power supply 6 supplies a RF power to the discharge electrode 4 via the matching circuit 5 thereby emitting a plasma from the discharge electrode 4.

The matching circuit 5 is provided to effect matching between the RF power supply 6 and reaction chamber 1 and to prevent reflected power from returning to the RF power supply 6 when forward power is supplied from the RF power supply 6 to discharge electrode 4, thereby stabilizing a plasma discharge.

FIG. 3 shows an equivalent circuit of the matching circuit. The matching circuit, as shown in the figure, comprises variable capacitors Ca and Cb and a variable coil L. A resistance Z is provided between the matching circuit 5 and a grounded inner wall 1a of the reaction chamber 1.

On the other hand, a waveguide window 7 formed of a dielectric material is provided on an upper part of the reaction chamber 1. A microwave generator 9 is connected to the waveguide window 7 via a microwave waveguide 8.

A tuner 10 is formed in the microwave waveguide 8, and a plurality of stubs 11 are inserted in the tuner 10. The positions of insertion of the stubs 11 are adjusted so that the tuner 10 may function to control microwaves.

A monitor 12 is connected between the discharge electrode 4 and matching circuit 5. The monitor 12 serves as physical quantity measuring means for measuring the physical quantity in the RF circuit for producing a plasma Q within the reaction chamber 1.

The monitor 12 measures, for example, a variation in reflected power within the reaction chamber 1 as the physical quantity in the RF circuit. The monitor 12 converts the measured variation value of reflected power to a voltage, digitizes the voltage, and outputs the resultant as a measurement signal.

An output terminal of the monitor 12 is connected to a computer 14 over a signal cable 13.

The computer 14 functions as plasma process end point determination means for receiving the measurement signal of reflected power from the monitor 12 and determining the plasma process end point on the basis of an inflection point of the reflected power relative to the passing of time.

A weighted moving averages section 15 has a function of passing the measurement signal of reflected power through the median filter and finding a weighted moving average in accordance with a Gauss distribution.

A determination section 16 finds a primary differential value or a secondary differential value of the value obtained by the averages section 15, and compares the found primary differential value or secondary differential value with a predetermined threshold value, thereby determining the plasma process end point.

The operation of the apparatus with the above-described structure will now be described.

The reaction chamber 1 is evacuated and a reaction gas such as an etching gas is supplied into the reaction chamber 1.

An RF power of, e.g. 300 to 1000 W is supplied from the RF power supply 6 to the discharge electrode 4 via the matching circuit 5, and the reaction gas present between the discharge electrode 4 and the grounded inner wall 1a of reaction chamber 1 is made into a plasma. Thus, the plasma etching process for the semiconductor wafer 3 placed within the reaction chamber 1 is performed.

The plasma Q may be produced within the reaction chamber 1 by guiding microwaves generated from the microwave generator 9 into the reaction chamber 1 via the microwave waveguide 8 as well as supplying the RF power from the RF power supply 6 to the discharge electrode 4.

Figure 4:
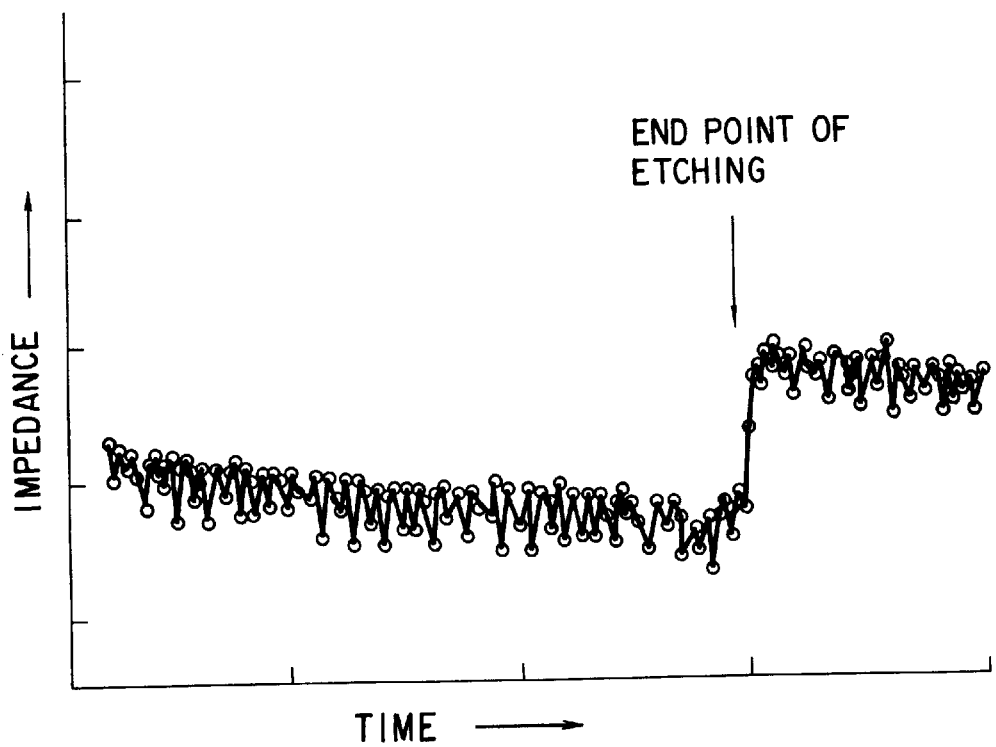
FIG. 4 is a graph showing an impedance variation within a reaction chamber at an etching end point.

It has turned out from experiments that at the end point of the etching process for the semiconductor wafer 3, the physical quantity in the RF circuit, e.g. the impedance of plasma Q, increases (or decreases) as shown in FIG. 4.

It has also turned out that at the end point of etching, other physical quantities in the RF circuit, such as voltage, current, reflection coefficient, voltage standing wave ratio, forward power, reflected power, effective power and reactive power, vary, too.

Accordingly, in the present apparatus, the plasma process end point is determined by detecting, e.g. the inflection point of variation of reflected power from the reactive chamber 1.

Specifically, the monitor 12 measures the reflected power varying due to an etching reaction within the reaction chamber 1, converts a value of a variation of the measured reflected power to a voltage, digitizes the voltage and outputs it as a measurement signal.

The computer 14 receives at a predetermined cycle the measurement signal of reflected power measured by the monitor 12 over the signal cable 13.

FIG. 5 shows an example of the waveform of the sampling value of the measured signal of reflected power, which was received in the computer 14. In fact, the waveform of the sampling value of reflected power is an aggregation of points of discrete values. For the purpose of convenience, however, the waveform is shown as a continuous curve. In the figures mentioned below, too, the waveform is shown as a continuous curve although it is actually the aggregation of points of discrete values.

The weighted moving averages section 15 of computer 14 passes the sampling value of the measurement signal through a general median filter and obtains a signal from which peculiar peaks have been removed, as shown in FIG. 6.

Suppose that the median-filtered sampling value at time t is S(t), as shown in FIG. 6. The computer 14 compares a predetermined threshold value H0 with the sampling value S(t), and determines a time t0, at which the condition of S(t)≧H0 is satisfied, to be an etching start time.

In addition, the computer 14 determines a time t1 (=t0+Td), which is delayed by a predetermined delay time Td, to be an arithmetic operation start time.

The weighted moving averages section 15 of computer 14 subjects the median-filtered sampling value S(t) to a weighted moving averaging process in accordance with a Gauss distribution.

If the sampling value obtained after the weighted moving averaging process is MWA(t), MWA(t) is given by $$MWA(t) = \sum_{n=-M}^{M} S(t - M - n) \cdot G(n) \quad (1)$$

The Gauss distribution G(x) is considered only in a range of −M≦x≦M with respect to a preset M. The Gauss distribution G(x) is expressed by $$G(x) = \frac{1}{\sqrt{2\pi}\,\sigma} \exp\left(-\frac{x^2}{2\sigma^2}\right) \approx \frac{4\sigma^{2C}x + 2\sigma^2}{2^{4\sigma^2}} \quad (2)$$

where σ is a preset standard deviation, and C is the number of a combination defined by $$_nC_k = \binom{n}{k} = \frac{n!}{(n-k)!\,k!} \quad (3)$$

FIG. 7 shows an example of the waveform of the thus obtained sampling value MWA(t) subjected to the weighted moving averaging process.

Subsequently, the determination section 16 performs a secondary differentiation of the sampling value MWA(t) obtained by the weighted moving averages section 15 and obtains a waveform D2(t) as shown in FIG. 8. The waveform D2(t) is expressed by $$D2(t) = MWA(t) - 2MWA(t-1) + MWA(t-2) \quad (4)$$

The determination section 16 then compares the waveform D2(5) with preset threshold values H1 and H2 and determines a time te, at which D2(t) satisfies the condition, D2(t)≧H1 or D2(t)≦H2, with respect to threshold values H1 and H2, to be an etching process end point.

The computer 14 finds a time from the etching start to the etching end point as a time te−t0.

The reason why the two threshold values H1 and H2 are provided is that there are an increasing variation and a decreasing variation of the sampling value S(t) at the etching end point.

The above-described arithmetic operations are carried out at the same time as the sampling of the measurement signal of reflected power, and the etching end point is determined in real time relative to the progression of etching.

As has been described above, in the first embodiment, the reflected power in the RF circuit for producing a plasma is measured, and the measurement signal of reflected power is passed through the median filter.

The measurement signal, which has been passed through the median filter, is subjected to the weighted moving averaging process in accordance with the Gauss distribution, and the secondary differential value of the resultant signal value is found and compared with the preset threshold values. Thereby the etching process end point is determined. Therefore, the etching end point can be exactly determined without influences of contamination on the plasma light intake window or variance of plasma light.

Moreover, since the weighted moving averaging process is carried out, a time lag in a case of performing a moving averaging process twice or more or an influence in a case where a signal variation is small can be suppressed. Thus, a small signal variation can be detected with a small time lag, and the etching end point can be exactly determined.

Second Embodiment

A plasma process end point determination apparatus according to a second embodiment of the present invention will now be described with reference to the accompanying drawings.

In this invention, when a plasma process end point is determined in a process in which a plasma is produced within the reaction chamber to process an object, a physical quantity in a circuit for producing the plasma is measured and the measurement signal of the physical quantity is passed through a median filter.

Then, auto-correlation coefficients of the measurement signal which has been passed through the median filter are found successively, and these auto-correlation coefficients are compared with a preset threshold value. Thus, the plasma process end point is determined.

Figure 9:
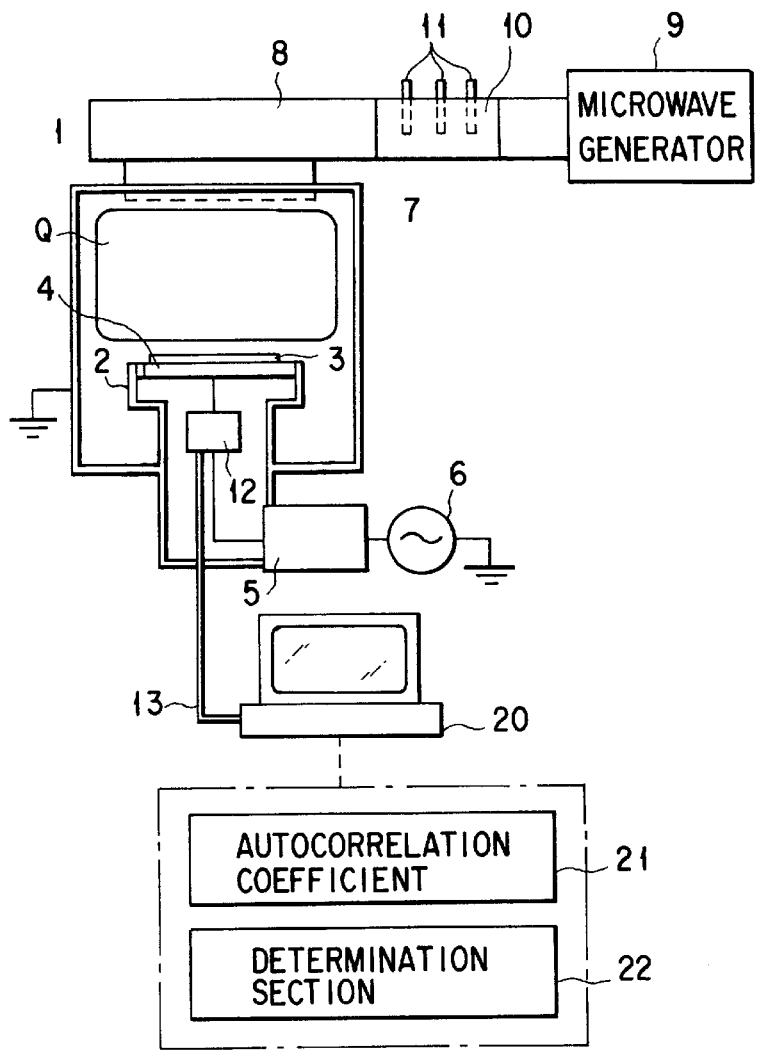
FIG. 9 shows a plasma process end point determination apparatus according to a second embodiment of the invention.

FIG. 9 shows the plasma process end point determination apparatus according to the second embodiment of the invention. The structural elements common to those in FIG. 2 are denoted by like reference numerals and a detailed description thereof is omitted.

A computer 20 functions as plasma process end point determination means for receiving the measurement signal of reflected power from the monitor 12 and determining the plasma process end point on the basis of an inflection point of the reflected power relative to the passing of time. The computer 20 has functions of an auto-correlation coefficient section 21 and a determination section 22.

The auto-correlation coefficient section 21 functions to pass the measurement signal of reflected power measured by the monitor 12 through the median filter and successively find auto-correlation coefficients.

The determination section 22 functions to each auto-correlation coefficient found by the auto-correlation coefficient section 21 with a preset threshold value, thereby determining the etching process end point.

The operation of the apparatus with the above structure will now be described.

A reaction gas such as an etching gas is supplied into the reaction chamber 1. An RF power of, e.g. 300 to 1000 W is supplied from the RF power supply 6 to the discharge electrode 4 via the matching circuit 5, and the reaction gas present between the discharge electrode 4 and the grounded inner wall 1a of reaction chamber 1 is made into a plasma. Thus, the plasma etching process for the semiconductor wafer 3 placed within the reaction chamber 1 is performed.

The plasma Q may be produced within the reaction chamber 1 by guiding microwaves generated from the microwave generator 9 into the reaction chamber 1 via the microwave waveguide 8 as well as supplying the RF power from the RF power supply 6 to the discharge electrode 4.

While the etching for the semiconductor wafer 3 is progressing, the monitor 12 measures the reflected power varying due to an etching reaction within the reaction chamber 1, converts a value of a variation of the measured reflected power to a voltage, digitizes the voltage and outputs it as a measurement signal.

The computer 20 receives at a predetermined sampling cycle the measurement signal of reflected power measured by the monitor 12 via the cable 13 and obtains a waveform of the sampling value of the measurement signal, as shown in FIG. 5. The auto-correlation coefficient section 21 of computer 20 passes the sampling value of the measurement signal through a general median filter and obtains a signal from which peculiar peaks have been removed, as shown in FIG. 6.

The auto-correlation coefficient section 21 finds the cycle of noise component in the median-filtered sampling value S(t) with respect to the waveform f(n) in preset time T0 by using an auto-correlation efficient $\Gamma ff(\tau)$.

In this case, T0=N0·Ts, where N0 is the number of times of sampling in time T0 and Ts is a sampling time.

The auto-correlation efficient $\Gamma ff(\tau)$ is expressed by $$\Gamma_{ff}(\tau) = \frac{\sum_n [(f(n) - \bar{f}) \cdot (f(n-\tau) - \bar{f}_\tau)]}{\sqrt{\sum_n (f(n) - \bar{f})^2 \cdot \sum_n (f(n-\tau) - \bar{f}_\tau)^2}} \quad (5)$$

where $\tau$ is a time error at the time of obtaining correlation.

$$\bar{f} = \frac{1}{N} \sum_{n=0}^{N-1} f(n) \quad (6)$$

$$\bar{f}_\tau = \frac{1}{N} \sum_{n=0}^{N-1} f(n-\tau) \quad (7)$$

where N=N0. In order to obtain the cycle of noise component, $$\tau=0 \ (\bar{f}=\bar{f}_{96}) \quad (8)$$

Figure 10:
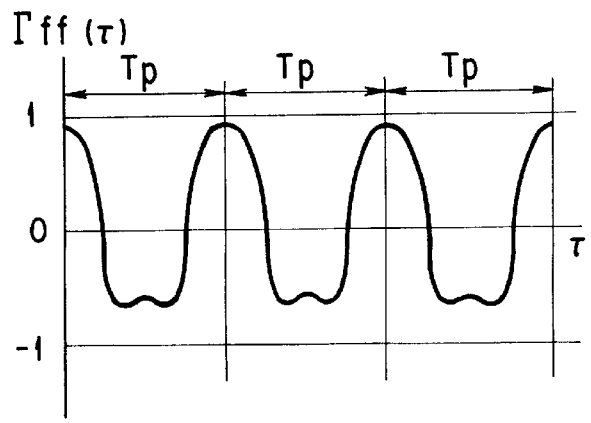
FIG. 10 shows an example of a graph of an auto-correlation coefficient Γff(τ) relative to a time point difference τ at the time of obtaining correlation.

FIG. 10 shows an example of the graph of auto-correlation efficient $\Gamma ff(\tau)$ relative to the time error $\tau$ at the time of obtaining correlation. The average value of time Tp between peaks is set at the cycle T of noise component.

Then, the auto-correlation coefficient section 21 performs an auto-correlation process for determining the etching end point. In this case, the time error is set at $\tau=\tau1$.

The end point determination start time t2 is expressed by $$t2 \approx t1+T0+T+\tau1 \quad (9)$$

where T=N1·Ts, and N1 is the number of times of sampling in time T.

Figure 11:
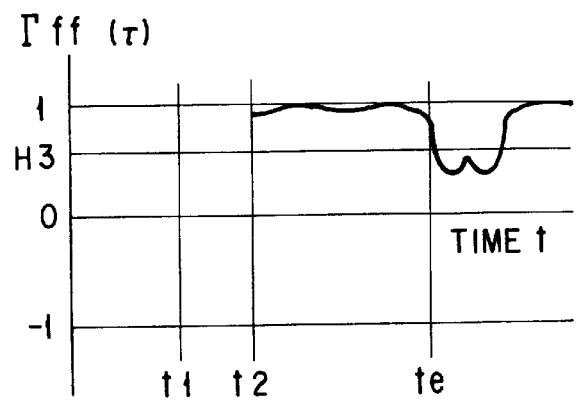
FIG. 11 shows an example of time dependency of auto-correlation coefficient Γff(τ)

Specifically, the auto-correlation coefficient section 21 performs the auto-correlation process for determining the etching end point with respect to the median-filtered sampling value S(t) shown in FIG. 6, with the value N set at N=N1. FIG. 11 shows an example of the graph (time-dependency of auto-correlation coefficient) of auto-correlation coefficient $\Gamma ff(\tau)$ obtained by the auto-correlation process.

The determination section 22 compares the auto-correlation coefficient $\Gamma ff(\tau)$ obtained by the auto-correlation coefficient section 21 and a preset threshold value H3 and determines a time te, at which the auto-correlation coefficient $\Gamma ff(\tau)$ satisfies the condition, $\Gamma ff(\tau) \leq H3$, with respect to threshold values H3, to be an etching process end point.

The above-described arithmetic operations are carried out at the same time as the sampling of the measurement signal of reflected power, and the etching end point is determined in real time relative to the progression of etching.

As has been described above, in the second embodiment, the reflected power in the RF circuit for producing a plasma is measured, and the measurement signal of reflected power is passed through the median filter. Thereafter, the auto-correlation coefficients are successively obtained and compared with the preset threshold values. Thereby the etching process end point is determined. Accordingly, like the first embodiment, the etching end point can be exactly determined without influences of contamination on the plasma light intake window or variance of plasma light.

Moreover, since the auto-correlation coefficients are used, a time lag in a case of performing a moving averaging process twice or more or an influence in a case where a signal variation is small can be suppressed. In particular, when a noise component has cyclicity, a small signal variation can be detected with a small time lag, and the etching end point can be exactly determined.

Third Embodiment

A third embodiment of the present invention will now be described with reference to the accompanying drawings. The structural elements common to those in FIG. 2 are denoted by like reference numerals and a detailed description thereof is omitted.

Figure 12:
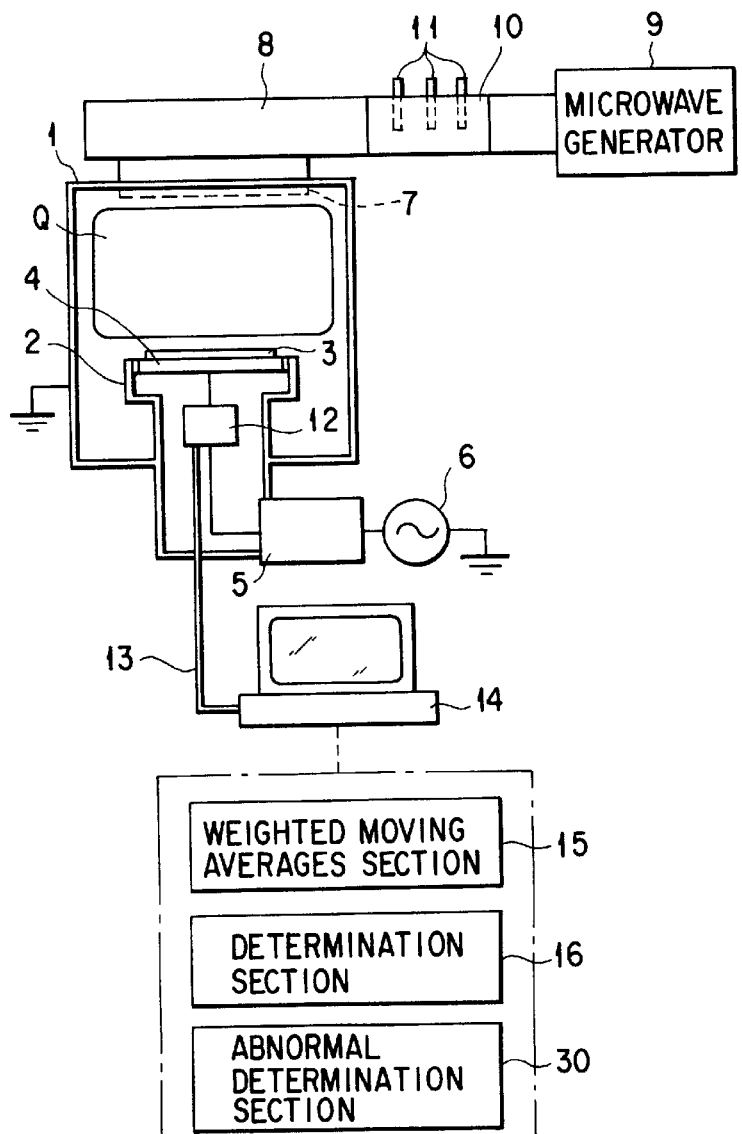
FIG. 12 shows a plasma process end point determination apparatus according to a third embodiment of the invention.

FIG. 12 shows a plasma process end point determination apparatus according to the third embodiment.

The computer 14 is provided with an abnormality determination section 30 in addition to the weighted moving averages section 15 and determination section 16.

The abnormality determination section 30 has functions of detecting a specific pattern variation, with the passing of time, of a measurement signal obtained by measuring reflected power in the RF circuit for producing a plasma, and determining, on the basis of the detected specific pattern variation, an abnormal discharge or a defect in the process for semiconductor wafer 3.

The operation of the apparatus with the above structure will now be described.

A reaction gas is supplied into the reaction chamber 1. An RF power is supplied from the RF power supply 6 to the discharge electrode 4 via the matching circuit 5, and the reaction gas present between the discharge electrode 4 and the grounded inner wall 1a of reaction chamber 1 is made into a plasma. Thus, the plasma etching process for the semiconductor wafer 3 placed within the reaction chamber 1 is performed.

While the etching for the semiconductor wafer 3 is progressing, the monitor 12 measures the reflected power varying due to an etching reaction within the reaction chamber 1, converts a value of a variation of the measured reflected power to a voltage, digitizes the voltage and outputs it as a measurement signal.

The computer 14 receives at a predetermined sampling cycle the measurement signal of reflected power measured by the monitor 12 via the cable 13 and obtains a waveform of the sampling value of the measurement signal, as shown in FIG. 5.

Like the first embodiment, the measurement signal of reflected power, which has been passed through the median filter, is subjected to the weighted moving averaging process in accordance with the Gauss distribution, and the secondary differential value of the resultant signal value is found and compared with the preset threshold values. Thereby the etching process end point is determined.

With respect to the sampling values of the measurement signal of reflected power, the abnormality determination section 30 calculates a difference between the currently acquired sampling value and an average value of one or more previously acquired sampling values, compares the difference with a preset value, and detects a specific pattern variation of the measurement signal with the passing of time.

For example, if an abnormal discharge of the plasma Q has occurred within the reaction chamber 1 or a defects has occurred in the process for the semiconductor wafer 3, such abnormality appears as specific pattern variation p1, p2 in the reflected power, for example, as shown in FIG. 13.

The abnormality determination section 30 detects such specific pattern variation p1, p2 and determines the occurrence of the abnormal discharge of plasma Q within the reaction chamber 1 or the defect in the process for semiconductor wafer 3.

The causes of abnormal discharge may be dust on the semiconductor wafer 3, short-circuit of wiring on the semiconductor wafer 3, degradation of components of the reaction chamber 1 (e.g. removal of alumite coating for insulation), etc.

As has been described above, according to the third embodiment of the invention, needless to say, the advantage of the first embodiment can be obtained. Moreover, the abnormality determination section 30 detects a specific pattern variation, with the passing of time, of a measurement signal obtained by measuring reflected power in the RF circuit for producing a plasma, and determines, on the basis of the detected specific pattern variation, an abnormal discharge of plasma Q or a defect in the process for semiconductor wafer 3.

In the third embodiment, the abnormality determination section 30 is provided in the computer 14 according to the first embodiment. However, it may be provided in the computer 20 according to the second embodiment so that an abnormal discharge of plasma Q or a defect in the process for semiconductor wafer 3 may be determined on the basis of the specific pattern variation.

The present invention is not limited to the first to third embodiments of the invention. These embodiments may be modified as follows.

For example, in the first to third embodiments, the reflected power is measured as physical quantity by using the monitor 12. However, one or more of the following physical quantities may be measured singly or in combination: impedance, voltage, current, reflection coefficient, voltage standing wave ratio, forward power, effective power, and reactive power in the RF circuit for producing the plasma.

If voltage is V, current is I, impedance in the RF circuit is Z, reflection coefficient is Γ and voltage standing wave ratio is VSWR, then resistance R, reactance X and reflection coefficient Γ have the following relationships:

$$R = Z \cos \theta \tag{10}$$

$$X = Z \sin \theta \tag{11}$$

$$\Gamma = (\Gamma r^2 + \Gamma i^2)^{1/2} \tag{12}$$

$$\Gamma r = (r^2 + x^2 - 1)/\{(r+1)^2 + X^2\} \Gamma i = 2x/\{(r+1)^2 + X^2\} r = R/Zo \; x = X/Zo$$

where Γr is a real number portion of the reflection coefficient, Γi is an imaginary number portion, and Zo is an impedance of signal cable 13, e.g. 50 Ω, which is set by the user.

The voltage standing wave ratio VSWR is expressed by $$VSWR = (1+\Gamma)/(1-\Gamma) \tag{13}$$

Accordingly, reflection coefficient Γ or voltage standing wave ratio VSWR may be calculated by measuring the impedance Z and phase θ of the RF circuit, and the etching end point may be determined by detecting the inflection point of the reflection coefficient Γ or voltage standing wave ratio VSWR.

An adjustment value of the variable capacitor Ca, Cb or variable coil L in the matching circuit 5 for matching the reaction chamber 1 with the RF power supply for producing plasma Q may be employed to determine the etching end point. Specifically, since the matching circuit 5 adjusts the variable capacitor Ca, Cb or variable coil L for matching with the RF circuit, the inflection point of the adjustment value of variable capacitor Ca, Cb or variable coil L at the etching end point can be detected by monitoring this adjustment value.

In the case where microwaves are introduced into the reaction chamber 1 to produce plasma Q, the insertion position of stubs 11 in the microwave waveguide 8 may be monitored and the etching end point may be detected from the variation in the insertion position.

In the first to third embodiments, the present invention is applied to the detection of the etching end point. However, this invention may be applied to automatic determination of the cleaning end point.

In the first to third embodiments, the detection point is the etching end point or cleaning end point. However, a certain time point after the detection may be determined as an end point.

As has been described above in detail, the present invention can provide a plasma process end point determination method capable of exactly determining a plasma process end point such as an etching end point, without influences of contamination on a plasma light take-in window or flickering of plasma light, and with less influences of a time delay occurring when moving averages are found twice or more or a signal variation is minute.

This invention can also provide a plasma process end point determination apparatus capable of exactly determining a plasma process end point such as an etching end point, without influences of contamination on a plasma light take-in window or flickering of plasma light, and with less influences of a time delay occurring when moving averages are found twice or more or a signal variation is minute.

Moreover, this invention can provide a plasma process end point determination apparatus capable of determining, on the basis of a detected specific pattern variation, an abnormal discharge of a plasma or a defect in a process for an object.

Fourth Embodiment

A plasma process end point determination apparatus according to a fourth embodiment of the invention will now be described with reference to the accompanying drawings.

FIG. 14 shows an etching end point determination apparatus (plasma process end point determination apparatus) applied to a magnetron RIE apparatus according to the fourth embodiment of the invention.

A lower electrode 102 is disposed in a lower part within a cylindrical reaction chamber 101. A semiconductor wafer 103 is placed on the lower electrode 102 as an object to be processed.

A projecting upper electrode 104 is formed at an upper portion of the reaction chamber 101. A gas reservoir 105 in which a reaction gas is supplied is formed inside the upper electrode 104. The upper electrode 104 is provided with a plurality gas jet holes 106 through which the reaction gas is fed into the reaction chamber 101.

An annular magnetron 107 is disposed around the reaction chamber 101 so as to be rotatable, for example, in a circumferential direction of the reaction chamber 101, which is indicated by an arrow. The magnetron 107 functions to produce a plasma 108 at a low pressure within the reaction chamber 101. The magnetron 107 is rotated at a predetermined rotational frequency by a rotation mechanism 109.

A radio-frequency power supply 111 is connected to the lower electrode 102 within the reaction chamber 101 via a matching box 110. The matching box 110 has a function of establishing matching between the RF power supply 111 and reaction chamber 101.

The matching box 110 includes a probe 112 and a matching circuit (MC) 113. The probe 112 serves as a detection section for monitoring a voltage and a current of RF power supplied to the reaction chamber 101 and outputting a monitor signal (detection signal).

A computer 114 receives and digitizes the monitor signal from the probe 112 and detects the end point of etching for the semiconductor wafer 103 within the reaction chamber 101 on the basis of the monitor output. The computer 114 has functions of a filter process section 115 and an etching end point determination section 116.

The filter process section 115 has a function of a low-pass filter for filtering the monitor signal from the probe 112 and passing a signal component with a frequency lower than the rotational frequency of the magnetron 107.

The function of the low-pass filter of the filter process section 115 is expressed by $$X(n) = b1 * Y(n) + b2 * Y(n-1) + b3 * Y(n-2) - a3 * X(n-2) - a2 * X(n-1) \quad (21)$$

where $Y(n)$ is RF voltage data, $X(n)$ is filtered data, $a2$, $a3$, $b1$, $b2$ and $b3$ are constants, and $n$ is the data number.

The low-pass filter ("first filter" hereinafter) has such characteristics that an overshoot once occurs at a rising portion of voltage and then the voltage is stabilized, as shown in FIGS. 15A and 15B. Thus, when the etching time is short, an etching end point cannot be detected. To cope with this problem, the filter process section 115 has a second process function as described below.

According to the second filter process function, an average value of voltage or current of RF power detected by the probe 112 is used in a predetermined time period at the rising of the filter output signal.

Specifically, in the second filter process function, equation (21) stated above is basically used and filtered output values of first $X(1)$ and second $X(2)$ of output $X(n)$ in equation (21) are averaged in a predetermined time period as shown in equation (22). Thereby the stabilization time after filtering is shortened.

$$X(m) = b1 * Y(m) + b2 * Y(m-1) + b3 * Y(m-2) - a3 * \Sigma Y(m-2)/(m-2) - a2 * \Sigma Y(m-1)/(m-1) \quad (22)$$

where $m$ is the data number, and $Y(m-1)/(m-1)$ is an average value of $m-1$ data.

For example, if RF voltage data corresponding to data numbers 1, 2, 3, . . . , n are V1, V2, V3, . . . , Vn, the outputs of the first and second filters are expressed by the following equations.

When the data number is 1 and voltage data V1, the first filter output $X(1)$ is expressed by $$X(1) = b1 * V(1) + b2 * (0) + b3 * (0) - a3 * (0) - a2 * (0) \quad (23)$$

When the data number is 2 and voltage data V2, the first filter output $X(2)$ is expressed by $$X(2) = b1 * V(2) + b2 * V(1) + b3 * (0) - a3 * (0) - a2 * V(1) \quad (24)$$

Similarly, $X(3)$, $X(4)$, . . . , $X(n)$ are expressed.

By contrast, as regards the second filter output, the filtered output values of first $X(1)$ and second $X(2)$ are averaged in a predetermined time period, as shown in equation (25). Thus, no filter output appears in connection with data numbers 1 and 2. As regards the next data number 3, when voltage data is V3, the third filter output $X(3)'$ is expressed by $$X(3)' = \text{ave}(V1, V2, V3) \text{ ave} \quad (25)$$

When the data number is 4 and voltage data is V4, the second filter output $X(4)'$ is expressed by $$X(4)' = \text{ave}(V2, V3, V4) \quad (26)$$

When the data number is 5 and voltage data is V5, the second filter output $X(5)'$ is expressed by $$X(5)'=b1*V5+b2*V4+b3*V3-X(4)'*a3-X(3)'*a2 \qquad (27)$$

Similarly, X(6)', X(7)', ..., X(n)' are expressed.

The etching end point determination section 116 includes a weighted moving averages section and a detection section (not shown) for detecting an end point of etching for semiconductor wafer 103 on the basis of a signal variation after filtering by the filter process section 115.

The operation of the apparatus with the above structure will now be described.

A reaction gas is supplied into the reaction chamber 101 and at the same time a radio-frequency power is supplied to the lower electrode 102 from the RF power supply 111.

The magnetron 107 is rotated by the rotation mechanism 109 around the outer periphery of the reaction chamber 101.

Thus the plasma 108 is produced at a low pressure within the reaction chamber 101. The semiconductor wafer 103 on the lower electrode 102 within the reaction chamber 101 is chemically reacted with ions and radicals in the plasma 108 and etched.

The etching process is thus carried out, and the amount of a reaction product produced in plasma 108 during etching or the amount of ions, radicals, etc. required for the reaction varies before and after the end point of the etching. Accordingly, the impedance of the plasma 108 varies.

The probe 112 monitors the voltage or current of RF power supplied to the reaction chamber 101, and outputs a monitor signal. The monitor signal is sent to the computer 114.

The computer 114 receives and digitizes the monitor output from the probe 112, and the filter process section 115 serving as the low-pass filter performs the first filter process for the monitor signal according to equation (21) and passes a signal component with a frequency lower than the rotational frequency of the magnetron 107.

FIGS. 15A and 15B show a radio-frequency voltage waveform of the signal component with the frequency lower than the rotational frequency of the magnetron 107, which has been passed through the low-pass filter, in relation to the etching time.

As has been described above, this RF voltage waveform has a less voltage variation due to magnetron 107 than the RF voltage waveform shown in FIG. 5, and a minute voltage variation near the etching end point can be detected.

Accordingly, the etching end point determination section 116 detects the signal variation after the filtering by the filter process section 115, for example, detects the FR voltage variation as shown in FIGS. 15A and 15B (enlarged view), and the weighted moving averages section subjects the data X(m) of the output signal to weighted moving averaging in accordance with the Gauss distribution. The data, which was subjected to the weighted moving averaging, is compared with two preset threshold values (one associated with a variation in the direction of increase and the other associated with a variation in the direction of decrease) in the detection section. A time point at which the data exceeds the threshold values is determined to be the end point of etching for the semiconductor wafer 103.

On the other hand, the first filter has such characteristics that an overshoot once occurs at a rising portion of voltage and then the voltage is stabilized, as shown in FIGS. 15A and 15B. Thus, when the etching time is short, an etching end point cannot be determined.

In such a case, according to the second filter process of the filter process section 115, an average value of voltage or current of RF power detected by the probe 112 is used in a predetermined time period at the rising of the filter output signal, as expressed in equation (22).

FIGS. 16A and 16B show an RF voltage waveform after the second filter process in relation to the etching time. The stabilization time after the filtering is decreased by using the average value of RF voltage in the predetermined time period at the rising of voltage.

Accordingly, even where the etching time is short, the etching end point determination section 116 detects the signal variation after the second filter process by the filter process section 115, for example, detects the FR voltage variation as shown in FIGS. 16A and 16B (enlarged view), and the weighted moving averages section subjects the data X(m) of the output signal to weighted moving averaging in accordance with the Gauss distribution.

The data, which was subjected to the weighted moving averaging, is compared with two preset threshold values (one associated with a variation in the direction of increase and the other associated with a variation in the direction of decrease) in the detection section. A time point at which the data exceeds the threshold values is determined to be the end point of etching for the semiconductor wafer 103.

In the above embodiment, the output signal from the filter process section 115 is subjected to the weighted moving averaging, and compared with the preset threshold values, thereby determining the etching end point. It is possible, however, to substitute an auto-correlation coefficient section for the weighted moving averages section, find successively auto-correlation coefficients from the output signal from the filter process section 115, and compare the auto-correlation coefficients with preset threshold values, thereby determining the etching end point.

In the fourth embodiment, as described above, either or both of the voltage and current of RF power supplied to the reaction chamber 101 are monitored by the probe 112.

The filter process section 115 of computer 114 filters the monitor signal and passes a signal component with a frequency lower than the rotational frequency of magnetron 107. On the basis of the signal variation after the filtering, the etching end point of the semiconductor wafer 103 is determined.

Accordingly, the etching end point can be exactly determined even if the impedance of plasma 108 is hidden by noise due to a rotation cycle of magnetron 107, which results from displacement of the plasma 108 due to the rotation of magnetron 107, the etching area is small and less than 10%, and a voltage variation at the etching end point is minute.

Moreover, according to the second filter process function, an average value of voltage or current of RF power detected by the probe 112 is used in a predetermined time period at the rising of the filter output signal. Thus, even if the output from the first filter overshoots at the time of rising and then stabilizes and the etching time is short, the etching end point can be exactly determined.

Fifth Embodiment

A plasma process end point determination apparatus according to a fifth embodiment of the invention will now be described. The structural elements common to those shown in FIG. 14 are denoted by like reference numerals, and a detailed description thereof is omitted.

FIG. 17 shows the structure of the etching end point determination apparatus as applied to a magnetron RIE apparatus, according to the fifth embodiment of the invention.

In this magnetron RIE apparatus, the magnetron 107 disposed around the reaction chamber 101 is replaced with a magnetron 120 which is rotatably disposed above the reaction chamber 101.

The magnetron 120 is rotated by a rotation mechanism 122 about its own axis 121 in the direction of an arrow with a predetermined rotational frequency.

With this structure, a reaction gas is supplied into the reaction chamber 101, a radio-frequency power is supplied to the lower electrode 102, and the magnetron 120 is rotated above the reaction chamber 101 at a predetermined rotational frequency.

Thus a plasma 108 is produced at a low pressure within the reaction chamber 101. The semiconductor wafer 103 is chemically reacted with ions and radicals in the plasma 108 and etched.

The probe 112 monitors the voltage or current of RF power supplied to the reaction chamber 101, and outputs a monitor signal.

Like the preceding embodiment, the computer 114 receives and digitizes the monitor output from the probe 112, and the filter process section 115 performs the first filter process for the monitor signal according to equation (21) and passes a signal component with a frequency lower than the rotational frequency of the magnetron 120.

The etching end point determination section 116 detects the signal variation after the filtering. For example, if the etching end point determination section 116 detects the FR voltage variation as shown in FIGS. 15A and 15B (enlarged view), it determines the end point of the etching for the semiconductor wafer 103.

On the other hand, according to the second filter process of the filter process section 115, when the etching time is short, the filter output is obtained by using the average value of the voltage or current of RF power detected by the probe 112 in a predetermined portion of the rising period of the filter output signal, as shown in equation (2).

Even where the etching time is short, the etching end point determination section 116 detects a signal variation after the second filter process by the filter process section 115. If it has detected the variation of the RF voltage, as shown in FIGS. 16A and 16B (enlarged view), the end point of the etching for the semiconductor wafer 103 is determined.

Accordingly, like the fourth embodiment, the etching end point can be exactly determined even if the impedance of plasma 108 is hidden by noise due to a rotation cycle of magnetron 107, which results from displacement of the plasma 108 due to the rotation of magnetron 107, the etching area is small and less than 10%, and a voltage variation at the etching end point is minute.

Even if the output from the first filter overshoots at the time of rising and then stabilizes and the etching time is short, the etching end point can be exactly determined.

The present invention is not limited to the fourth and fifth embodiments, and the following modifications may be made.

In the fourth and fifth embodiments, in the second filter, the filtered output values of first X(1) and second X(2) are averaged in a certain period, as shown in equation (2). However, the values of first X(1) through a given output X(k) may be averaged.

The processing in the filter process section 115 is not limited to that based on the software by the computer 114. A low-pass filter comprising a coil, a resistor, etc. may be connected between the probe 12 and computer 114.

As has been described above, the present invention can provide a plasma process end point determination method and apparatus capable of determining the process end point without influence of noise due to the rotation of the magnetron.

Sixth Embodiment

A sixth embodiment of the invention will now be described with reference to the accompanying drawings.

FIG. 18 shows a plasma evaluation apparatus to which a plasma evaluation method of the present invention is applied.

In FIG. 18, numeral 301 denotes a reaction chamber, and the inside thereof is sealed. Although not shown, the reaction chamber 301 is provided with a process gas supply section for supplying a process gas for etching, etc. into the chamber 301 and an exhaust section for exhausting a reaction gas, etc. within the reaction chamber 301. A table 302 with a discharge electrode 304, on which a semiconductor wafer 303 may be placed as an object to be processed, is provided in a bottom portion of the reaction chamber 301.

A radio-frequency power supply 307 is connected to the discharge electrode 304 via a monitor 305 serving as a physical quantity measuring section (described later) and a matching circuit 306, whereby a plasma producing circuit (an RF circuit) is constituted. If power is supplied from the RF power supply 307 to the discharge electrode 304, a discharge occurs between the discharge electrode 304 and the inner walls of the reaction chamber 301 and the process gas supplied in the reaction chamber 301 is activated and made into a plasma.

The matching circuit 306 establishes matching between the RF power supply 307 and reaction chamber 301, prevents reflected power from returning to the RF power supply 307 when power is supplied from the RF power supply 307 to the discharge electrode 304, and stabilizes the plasma discharge. As is shown in FIG. 19, the matching circuit 306 comprises variable capacitors Ca and Cb and variable coil L. A load Z is provided between the matching circuit 306 and a grounded inner wall 301a of reaction chamber 301.

The monitor 305 provided between the discharge electrode 304 and RF power supply 307 serves as physical quantity measuring means for measuring a physical quantity in the RF circuit for producing the plasma Q within the reaction chamber 301. The physical quantity measured by the monitor 305 is, for example, an impedance in the RF circuit, voltage, current, reflection coefficient, voltage standing wave ratio, forward power, reflected power, effective power, or reactive power.

A computer 308 serving as comparison/evaluation means is connected to the monitor 305. The computer 308 converts a variation of a measured physical quantity, such as an impedance, to a voltage, digitizes the voltage, and outputs a digital measurement signal. The computer 308 has a function of receiving the measurement signal of the physical quantity measured by the monitor 305 and determining whether it is within a preset range.

The plasma evaluation method of this invention will now be described on the basis of the apparatus having the above structure.

If a process of etching or ashing is performed on an object for a long time, films will form on the electrode, the components of the electrode, the inner walls of the reaction chamber, etc., and the electrode and the components of the electrode will deteriorate. Consequently, a uniform plasma process cannot be performed. To solve this problem, the reaction chamber and electrode are disassembled after a predetermined time period, the formed films are washed away or the structural components are exchanged, and then the reaction chamber and electrode are reassembled.

After the plasma apparatus is reassembled, air is exhausted from the inside of the reaction chamber 301, a reaction gas such as an etching gas is supplied into the reaction chamber 301, and the pressure within the reaction chamber 301 is maintained at a predetermined level for the process. After the pressure within the reaction chamber 301 is stabilized, an RF power of, e.g. 300 to 1000 W is supplied from the RF power supply 307 to the discharge electrode 304 via the matching circuit 306. Then, the plasma Q is produced between the discharge electrode 304 and the inner walls of the reaction chamber 301.

The monitor 305 detects a variation in a physical quantity in the RF circuit which results from the production of the plasma Q, for example, a variation in impedance of the plasma Q. Apart from the impedance of plasma Q, the physical quantity in the RF circuit may be, for example, a voltage, current, reflection coefficient, voltage standing wave ratio, forward power, reflected power, effective power, or reactive power.

Figure 20:
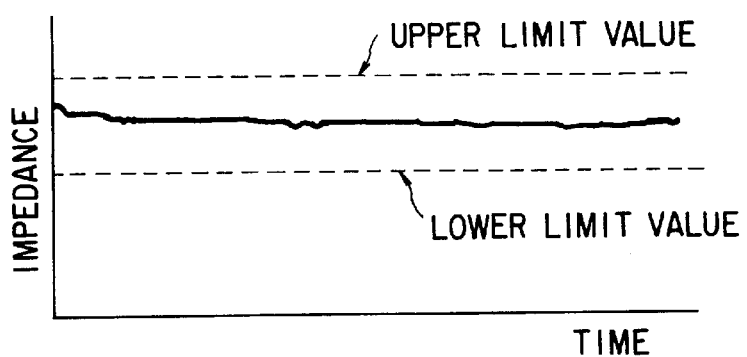
FIG. 20 is a graph showing a waveform indicating a state in which an impedance value is within a predetermined range.
Figure 21:
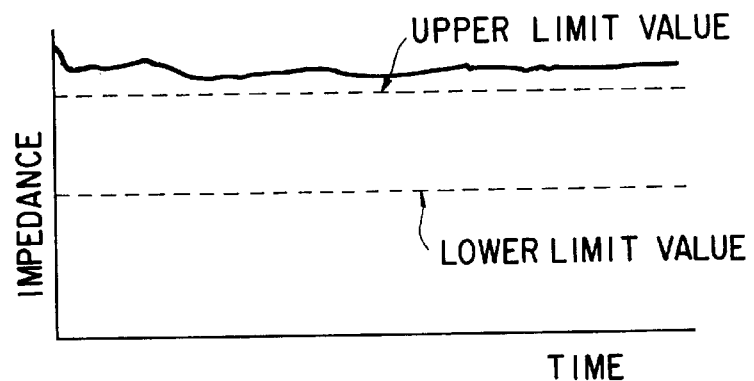
FIG. 21 is a graph showing a waveform indicating a state in which an impedance value exceeds an upper limit value.
Figure 22:
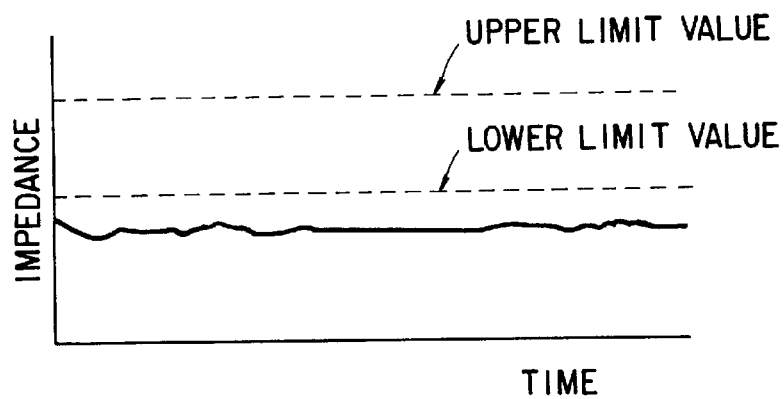
FIG. 22 is a graph showing a waveform indicating a state in which an impedance value descends below a lower limit value.

The monitor 305 converts the detected value of a variation of impedance due to the production of the plasma Q within the reaction chamber 301 to a voltage signal, digitizes the voltage signal, and outputs the digital voltage signal as a measurement signal to the computer 308 serving as comparison/evaluation section. FIGS. 20 to 22 show waveforms of the measurement signal obtained at this time. In fact, the waveforms of the signal are aggregations of points of discrete values. For the purpose of convenience, however, the waveforms are shown as continuous curves.

The computer 8 receives the measurement signal transmitted from the monitor 305 and determines whether the variation in impedance of the signal lies between preset upper limit and lower limit values. If the measurement signal exceeds the upper limit value, as shown in FIG. 21, or falls below the lower limit value, as shown in FIG. 22, it is determined that the assembly is not exactly made.

On the basis of the determination result, the operator reassembles and adjusts the reaction chamber 301 and electrode so that the variation in impedance of the plasma Q falls within the predetermined range.

The upper limit and lower limit values to be compared with the measurement signal sent from the monitor 305 are determined on the basis of the condition under which an optimal plasma Q was produced. However, these limit values may be determined, for example, on the basis of the condition before the disassembly/reassembly if the same process performance as before the disassembly/reassembly needs to be obtained.

As has been described above, according to the sixth embodiment of the invention, a plasma is produced after disassembly/reassembly of the reaction chamber, electrode, etc., and the variation in the physical quantity due to the plasma is directly detected in order to evaluate the plasma produced after the reassembly. Thus, a direct determination, and not an indirect determination using a sample, can be performed. Moreover, since there is no need to perform a plasma process for the sample, the condition of the plasma can be evaluated with no time consumed for the process for the sample.

Since the sample is exposed to the plasma only in a time period for measuring the variation in physical quantity due to the production of plasma, the cost is reduced as compared to the prior art in which one sample is needed for each measuring operation.

An adjustment value of variable capacitor Ca, Cb or variable coil L in the matching circuit for establishing the matching between the reaction chamber 301 and the RF power supply for producing plasma Q may be used as the physical amount as a basis for evaluation of the produced plasma. Specifically, in the matching circuit 305, the variable capacitor Ca, Cb or variable coil L is adjusted for matching with the RF circuit. Thus, if the adjustment value of the variable capacitor Ca, Cb or variable coil L is detected and compared with a predetermined value, the reproducibility of the plasma can be evaluated.

As has been described above in detail, the present invention can provide a plasma evaluation method and apparatus which is efficient in time and cost and can evaluate the plasma in the reaction chamber directly from the physical quantity in the plasma producing circuit or matching circuit, and not indirectly with use of the process for the sample.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A plasma process end point determination method, comprising the steps of:
    measuring a physical quantity in a circuit for producing a plasma within a reaction chamber; and
    determining a plasma process end point on the basis of an inflection point of the measured physical quantity in relation to the passing of time.

2. The plasma process end point determination method according to claim 1, wherein said step of determining the plasma process end point comprises the steps of:
    passing a measurement signal of the measured physical quantity through a median filter;
    subjecting the measurement signal, which is passed through the median filter, to weighted moving averaging in accordance with a Gauss distribution;
    finding one of a primary differentiation value and a secondary differentiation value of the measurement signal subjected to the weighted moving averaging; and
    comparing one of the found primary and secondary differentiation values with a preset threshold value, thereby determining the plasma process end point.

3. The plasma process end point determination method according to claim 1, wherein said step of determining the plasma process end point comprises the steps of:
    passing a measurement signal of the measured physical quantity through a median filter;
    successively finding auto-correlation coefficients of the measurement signal passed through the median filter; and
    comparing the found auto-correlation coefficients with a preset threshold value, thereby finding the plasma process end point.

4. The plasma process end point determination method according to claim 1,
    wherein the circuit comprises:
        a discharge electrode provided in the reaction chamber;
        a radio-frequency power supply; and
        a matching circuit for matching between the discharge electrode and the radio-frequency power supply.

5. A plasma process end point determination apparatus, comprising:
    physical quantity measurement means for measuring a physical quantity in a circuit for producing a plasma within the reaction chamber; and
    plasma process end point determination means for determining a plasma process end point on the basis of an inflection point of the physical quantity measured by the physical quantity measurement means in relation to the passing of time.

6. The plasma process end point determination apparatus according to claim 5, wherein said physical quantity measuring means uses at least one of an impedance, a voltage, a current, a reflection coefficient, a voltage standing wave ratio, a forward power, a reflected power, an effective power and a reactive power in the circuit for producing the plasma, an adjustment value of a variable capacitor for matching the reaction chamber with a radio-frequency power supply for producing the plasma, an adjustment value of the variable coil, and a position of a stub in a waveguide for connecting the reaction chamber and a microwave circuit for producing the plasma.

7. The plasma process end point determination apparatus according to claim 5, wherein said plasma process end point determination means comprises:
- a weighted moving averages section for passing a measurement signal of the measured physical quantity through a median filter, and finding a weighted moving average in accordance with a Gauss distribution; and
- a determination section for finding one of a primary differentiation value and a secondary differentiation value of the average found by the weighted moving averages section, and comparing said one of the found primary and secondary differentiation values with a preset threshold value, thereby determining the plasma process end point.

8. The plasma process end point determination apparatus according to claim 5, wherein said plasma process end point determination means comprises:
- an auto-correlation coefficient section for passing a measurement signal of the measured physical quantity through a median filter, and successively finding auto-correlation coefficients; and
- a determination section for comparing the auto-correlation coefficients found by the auto-correlation coefficient section with a preset threshold value, thereby finding the plasma process end point.

9. The plasma process end point determination apparatus according to claim 5, further comprising:
- abnormality determination means for detecting a specific pattern variation of a measurement signal of the physical quantity in relation to the passing of time, and determining abnormality of the plasma process on the basis of the detected specific pattern variation.

10. The plasma process end point determination method according to claim 5,
- wherein the circuit comprises:
  - a discharge electrode provided in the reaction chamber;
  - a radio-frequency power supply; and
  - a matching circuit for matching between the discharge electrode and radio-frequency power supply.

11. A plasma process end point determination method, comprising the steps of:
- detecting a physical quantity in a circuit for generating a plasma within the reaction chamber as a detection signal;
- filtering the detection signal and passing a component of the detection signal, which has a frequency lower than a rotational frequency of a magnetron; and
- determining an end point of a plasma process for an object on the basis of a signal variation of the filtered detection signal.

12. The plasma process end point determination method which makes a plasma generate in a reaction chamber to process an object, according to claim 11, wherein in the step of determining the end point of the plasma process an average value of one of the voltage and current of the radio-frequency power is used for that portion of the filtered detection signal, which is obtained in a predetermined period at a start of operation of the filter.

13. The plasma process end point determination method according to claim 11, wherein in the step of determining the end point of the plasma process, the filtered detection signal is subjected to weighted moving averaging in accordance with a Gauss distribution, and one of primary and secondary differential values of the detection signal subjected to the weighted moving averaging is found and compared to a preset threshold value, whereby the end point of the plasma process is determined.

14. The plasma process end point determination method according to claim 11, wherein in the step of determining the end point of the plasma process, auto-correlation coefficients are successively found from the filtered detection signal and compared to a preset threshold value, whereby the plasma process end point is determined.

15. The plasma process end point determination method according to claim 11,
- wherein the physical quantity is at least one of a voltage and a current of radio frequency power supplied to the reaction chamber.

16. A plasma process end point determination method according to claim 11,
- wherein the circuit comprises:
  - a discharge electrode provided in the reaction chamber;
  - a radio-frequency power supply; and
  - a matching circuit for matching between the discharge electrode and the radio-frequency power supply.

17. A plasma process end point determination apparatus, comprising:
- detection means for detecting a physical quantity in a circuit for generating a plasma within the reaction chamber as a detection signal;
- filter process means for filtering the detection signal detected by the detection means and passing a portion of the detection signal which has a frequency lower than a rotational frequency of a magnetron; and
- plasma end point determination means for determining an end point of a plasma process for an object on the basis of a variation of the detection signal filtered by the filter process means.

18. The plasma process end point determination apparatus according to claim 17, wherein the filter process means uses an average of one of a voltage and a current of the radio-frequency power for the filtered detection signal in a predetermined period of rising.

19. The plasma process end point determination apparatus according to claim 17, wherein said filter process means is a low-pass filter.

20. The plasma process end point determination apparatus according to claim 17, wherein said plasma process end point determination means comprises:
- weighted moving averaging means for finding a weighted moving average in accordance with a Gauss distribution on the basis of the detection signal filtered by the filter process means; and
- determination means for determining the end point of the plasma process by finding one of primary and secondary differential values of the weighted moving average obtained by the weighted moving averaging means and comparing the found one of primary and secondary differential values with a preset threshold value.

21. The plasma process end point determination apparatus according to claim 17, wherein said plasma process end point detection means comprises:

auto-correlation coefficient means for successively finding auto-correlation coefficients from the detection signal filtered by the filter process means; and determination means for determining the plasma process end point by comparing each auto-correlation coefficient found by the auto-correlation coefficient means with a preset threshold value.

22. The plasma process end point determination apparatus according to claim 17, wherein the physical quantity is at least one of a voltage and a current of radio-frequency power supplied to the reaction chamber.

23. The plasma process end point determination apparatus according to claim 17, wherein the circuit comprises:
a discharge electrode provided in the reaction chamber;
a radio-frequency power supply; and
a matching circuit for matching between the discharge electrode and the radio-frequency power supply.

24. A plasma evaluation method, comprising the steps of:
detecting a physical quantity in a circuit for producing a plasma within a reaction chamber; and
comparing the detected physical quantity with a preset value, thereby evaluating the condition of produced plasma.

25. The plasma evaluation method according to claim 24, wherein the step of detecting the physical quantity is performed after a plasma process apparatus is assembled.

26. The plasma evaluation method according to claim 24, wherein said physical quantity comprises at least one of an impedance, a voltage, a current, a reflection coefficient, a voltage standing wave ratio, a forward power, a reflected power, an effective power and a reactive power in said circuit.

27. The plasma evaluation method according to claim 24, wherein the circuit comprises:
a discharge electrode provided in the reaction chamber;
a radio-frequency power supply; and
a matching circuit for matching between the discharge electrode and the radio-frequency power supply.

28. A plasma evaluation apparatus, comprising:
a plasma producing circuit for producing a plasma within the reaction chamber;
physical quantity measuring means for measuring a physical quantity in the plasma producing circuit; and
evaluation means for evaluating the condition of the produced plasma by comparing the physical quantity measured by the physical quantity measuring means with a preset value.

29. The plasma evaluation apparatus according to claim 28, wherein the physical quantity measuring means uses at least one of an impedance, a voltage, a current, a reflection coefficient, a voltage standing wave ratio, a forward power, a reflected power, an effective power and a reactive power in the circuit for producing the plasma.

30. A plasma evaluation apparatus comprising:
a plasma producing circuit for generating a plasma within a reaction chamber;
a matching circuit for establishing matching between the plasma producing circuit and the reaction chamber;
physical quantity measuring means for measuring a physical quantity in the matching circuit; and
evaluation means for evaluating the condition of the produced plasma by comparing the physical quantity measured by the physical quantity measuring means with a preset value.

31. The plasma evaluation apparatus according to claim 30, wherein said matching circuit comprises a variable capacitor and a variable coil, and the physical quantity comprises values of the variable capacitor and the variable coil.

32. The plasma evaluation apparatus according to claim 30, wherein the circuit comprises:
a discharge electrode provided in the reaction chamber;
a radio-frequency power supply; and
a matching circuit for matching between the discharge electrode and the radio-frequency power supply.

* * * * *